US006458163B1

(12) United States Patent
Slemker et al.

(10) Patent No.: US 6,458,163 B1
(45) Date of Patent: Oct. 1, 2002

(54) COUPLING-SOCKET ADAPTER ASSEMBLY FOR A PROSTHETIC LIMB

(75) Inventors: Tracy C. Slemker, Clayton; Lanny K. Wiggins, Miamisburg; Scott R. Schall, Clayton, all of OH (US)

(73) Assignee: Prosthetic Design, Inc., Clayton, OH (US)

( * ) Notice: Subject to any disclaimer, the term of this patent is extended or adjusted under 35 U.S.C. 154(b) by 0 days.

(21) Appl. No.: 09/613,977

(22) Filed: Jul. 11, 2000

(51) Int. Cl.[7] .................................................. A61F 2/80
(52) U.S. Cl. ......................................................... 623/38
(58) Field of Search ..................................... 623/33, 38

(56) References Cited

U.S. PATENT DOCUMENTS

| 3,659,294 | A |   | 5/1972  | Glabiszewski ................... 3/21 |
| 4,007,496 | A |   | 2/1977  | Glabiszewski ..................... 3/2 |
| 4,536,898 | A |   | 8/1985  | Palfray ........................ 623/33 |
| 4,608,054 | A | * | 8/1986  | Schroder ...................... 623/39 |
| 4,795,474 | A |   | 1/1989  | Horvath ....................... 623/27 |
| 4,938,775 | A |   | 7/1990  | Morgan ........................ 623/27 |
| 4,969,911 | A |   | 11/1990 | Greene ........................ 623/38 |
| 5,047,063 | A |   | 9/1991  | Chen .......................... 623/38 |
| 5,163,965 | A |   | 11/1992 | Rasmusson et al. ........... 623/36 |
| 5,376,129 | A |   | 12/1994 | Faulkner et al. .............. 623/33 |
| 5,425,782 | A | * | 6/1995  | Phillips ....................... 623/38 |
| 5,443,526 | A |   | 8/1995  | Hoerner ....................... 623/38 |
| 5,458,657 | A |   | 10/1995 | Rasmusson .................... 623/38 |
| 5,482,513 | A |   | 1/1996  | Wilson ........................ 623/52 |
| 5,507,837 | A |   | 4/1996  | Laghi ......................... 623/38 |
| 5,529,576 | A |   | 6/1996  | Lundt et al. .................. 623/38 |
| 5,545,230 | A |   | 8/1996  | Kinsinger et al. ............. 623/38 |
| 5,549,710 | A |   | 8/1996  | Vera et al. ................... 623/38 |
| 5,759,206 | A |   | 6/1998  | Bassett ....................... 623/38 |
| 6,013,105 | A | * | 1/2000  | Potts ......................... 623/38 |
| 6,033,440 | A | * | 3/2000  | Schall et al. ................. 623/38 |
| 6,231,618 | B1| * | 5/2001  | Schall et al. ................. 623/38 |

FOREIGN PATENT DOCUMENTS

| CH | 638095   | 9/1980  |
| DE | 3937379  | 5/1991  |
| EP | 610124   | 1/1994  |
| FR | 2410998  | 12/1977 |
| FR | 2630641  | 5/1988  |
| GB | 1208421  | 10/1970 |
| JP | 8089519  | 4/1996  |
| JP | 8294504  | 11/1996 |
| RU | 1109152  | 8/1984  |
| RU | 1217404  | 3/1985  |
| RU | 1553115  | 3/1990  |

OTHER PUBLICATIONS

Otto Bock, *Double and Eccentric Adapters*, Otto Bock Orthopedic Industry, 1993.
*Prosthetic Alignment Device*, NSF 1997 Engineering Senior Design Projects to Aid Persons with Disabilities, 1997.
Attachment A represents a Prior Art commercially available component assembly.

* cited by examiner

*Primary Examiner*—Bruce Snow
(74) *Attorney, Agent, or Firm*—Taft, Stettinius & Hollister LLP

(57) ABSTRACT

A coupling-socket adapter assembly for a prosthetic limb. A base plate subassembly is attachable to a first prosthetic limb component. A coupling-socket adapter is rotatably attached to the base plate subassembly and has a cavity for receiving a male coupling member (such as a boss of a pyramidal link-plate). Various mechanisms, including a ring having internal threads and including a ring-clamp, are disclosed for locking the coupling-socket adapter against rotation with respect to the base plate subassembly and for unlocking the coupling-socket adapter for rotation with respect to the base plate subassembly, wherein the mechanisms are operable when the base plate subassembly is attached to the first prosthetic limb component.

17 Claims, 8 Drawing Sheets

COUPLING-SOCKET ADAPTER ASSEMBLY FOR A PROSTHETIC LIMB

BACKGROUND OF THE INVENTION

The present invention relates generally to prosthetic devices, and more particularly to a prosthetic-limb coupling-socket adapter which secures a boss of a prosthetic-limb link-member.

As shown in FIG. 1a, a conventional pyramidal link-plate 10 is one type of prosthetic-limb link-member and has a frustopyramidal, four-sided boss 12 projecting from a dome-shaped, or a spherically-convex-shaped, base 14, which in turn projects from a plate member 16. The plate member 16 will typically include four screw or bolt-receiving, through-holes 18 corresponding to a standard (within the industry) four-hole pattern.

As shown in FIG. 1b, a prosthetic limb 20 for a trans-femoral amputee will include a prosthetic limb socket 22 for receiving the wearer's residual limb, a knee joint assembly 24, a first pylon component 23 between the prosthetic limb socket and the knee joint assembly, interconnection components 26 for coupling the first pylon 23 to the prosthetic limb socket 22, interconnection components 27 for coupling the first pylon to the knee joint assembly 24, an ankle/foot assembly 28, and a second pylon 29 coupled between the knee joint assembly 24 and the ankle/foot assembly 28. The interconnection components 26 may consist of a locking or suction assembly 30 (such as a Shuttle Lock component or a ProSeal component commercially available from Prosthetic Design, Inc.) positioned within a distal end of the prosthetic limb socket 22, the conventional pyramidal link-plate 10, and a conventional coupling-socket adapter 32 for coupling the first pylon 23 to the distal boss 12 of the pyramidal link-plate 10. Likewise, the interconnection components 27 may consist of another conventional pyramidal link-plate 10 mounted to the knee-joint assembly and another conventional coupling-socket adapter 32 for coupling the first pylon 23 to the distal boss 12 of the pyramidal link-plate 10. A plurality of set screws 33 extend radially and downwardly against the distal boss 12 of the pyramidal link-plate 10 and are tightened to securely mount the pyramidal link-plate 10 (and the respective prosthetic limb components fastened thereto) to the coupling-socket adapter 32 (and the first pylon 23). The conventional pyramidal link-plate 10 and the conventional coupling-socket adapter 32 are primarily based upon the "Adjustable Link" described in U.S. Pat. No. 3,659,294 to Glabiszewski, the disclosure of which is incorporated herein by reference.

In fitting prosthetic limbs to patients, it is often necessary for the prosthetist to modify the alignments and orientations of the various prosthetic limb components with respect to each other during the initial fitting or after the patient has worn the prosthetic limb for a period of time. The first pylon 23 is typically capable of being rotatably adjusted with respect to the coupling-socket adapters. However, with certain transfemoral amputees, the distance between the distal end of the patient's residual limb and the patient's natural knee center is very short; and if the combined length of the components between a prosthetic limb socket and the prosthetic knee joint is greater than the distance between the distal end of the patients residual limb and the patient's natural knee center, then the prosthetist may be forced to eliminate the first pylon 23. Otherwise the knee center on the prosthetic side will be too low, thus causing gate deviation.

When the first pylon 23 is eliminated, the means to rotatably adjust the various prosthetic limb components is also lost. Accordingly, there are existing pyramidal link-plate components which offer sliding and/or rotating capabilities to such components. The disadvantage with the conventional sliding and/or rotating pyramidal link-plate components is that, to provide such adjustability, the profile and/or the length of the component must be increased. Other rotatably adjustable pyramidal link-plate components only allow finite or incremental rotation and are difficult to adjust.

For example, one known rotatably adjustable pyramidal link-plate assembly includes a dome shaped component having the pyramidal boss extending from its apex, where the dome shaped component includes an upwardly facing (i.e., facing in towards the apex of the dome), serrated, annular ring positioned around an outer circumference of the base of the dome. The assembly also includes a planar base plate component having four screw-holes extending therethrough and arranged in a standard four-hole pattern. The planar base plate also has a central hole sized for receiving the dome portion of the dome shaped component therethrough. On the underside of the planar base plate, encircling the central hole, is a serrated, annular ring adapted to engage with the upwardly facing serrated, annular ring of the dome shaped component when the dome shaped component is inserted through the underside of the central hole. When the two components are assembled, and installed onto a prosthetic limb component by tightening four screws extending through the screw-holes, the two components are rotationally locked with respect to each other. To rotatably adjust the two components with respect to each other, the four screws must be loosened enough to allow the base plate component to be lifted from the dome shaped component to a sufficient extent so that the two serrated rings disengage from one another. Once the rotational adjustment is made, the screws are tightened again.

One disadvantage with this design is that the serrations, or teeth, allow for only finite (e.g. 5 or 6 degree increments) rotational adjustments. Additionally, it is often-times difficult to have access to the four screws extending through the base plate component (especially when the prosthetic limb socket and knee joint assembly are positioned in close proximity to one another). To access the four screws in such a situation, the adjustable pyramid link-plate assembly must first be separated from the female coupling-socket adapter. Accordingly the prosthetist will essentially have to disassemble the prosthetic limb to adjust rotational alignment.

Accordingly, there is a need for a prosthetic-limb coupling-socket adapter assembly that provides rotatable adjustment for the prosthetic limb, yet does not significantly increase the profile or length of the attachment of the interconnection components. There also is a need for a prosthetic-limb coupling-socket adapter assembly that provides for infinite rotational adjustments. There further is a need for a prosthetic-limb coupling-socket adapter assembly that does not require disassembly of the various interconnection components to allow for rotational adjustments.

SUMMARY OF THE INVENTION

In a first statement of the coupling-socket adapter assembly of the invention, the coupling-socket adapter assembly is for a prosthetic limb and includes a base plate subassembly, a coupling-socket adapter, and a rotational locking and unlocking mechanism. The base plate subassembly is attachable to a first prosthetic limb component. The coupling-socket adapter is rotatably attached to the base plate subassembly and has a cavity for receiving a male coupling member (such as a boss of a pyramidal link-plate). The mechanism locks the coupling-socket adapter against rotation with respect to the base plate subassembly and unlocks the coupling-socket adapter for rotation with respect to the base plate subassembly. The mechanism is operable when the base plate subassembly is attached to the first prosthetic limb component.

In a second statement of the coupling-socket adapter assembly of the invention, the coupling-socket adapter assembly is for a prosthetic limb and includes a base plate subassembly, a coupling-socket adapter, and a ring. The base plate subassembly is attachable to a first prosthetic limb component. The coupling-socket adapter is rotatably attached to the base plate subassembly, has an upper portion and a lower portion, and has a cavity for receiving a male coupling member (such as a boss of a pyramidal link-plate). The ring surrounds the lower portion of the coupling-socket adapter, is positioned between the base plate subassembly and the upper portion of the coupling-socket adapter, and is threadably engaged with the base plate subassembly or the coupling-socket adapter or both. Rotation of the ring locks the coupling-socket adapter against rotation with respect to the base plate subassembly, and counterrotation of the ring unlocks the coupling-socket adapter for rotation with respect to the base plate subassembly.

In a third statement of the coupling-socket adapter assembly of the invention, the coupling-socket adapter assembly is for a prosthetic limb and includes a base plate subassembly, a coupling-socket adapter, and a ring. The base plate subassembly is attachable to a first prosthetic limb component. The coupling-socket adapter is rotatably attached to the base plate subassembly, has an upper portion and a lower portion, and has a cavity for receiving a male coupling member (such as a boss of a pyramidal link-plate). The ring surrounds, and is threadably attached to, the lower portion of the coupling-socket adapter, and the ring is positioned between the base plate subassembly and the upper portion of the coupling-socket adapter. Rotation of the ring with respect to the coupling-socket adapter locks the coupling-socket adapter against rotation with respect to the base plate subassembly, and counterrotation of the ring with respect to the coupling-socket adapter unlocks the coupling-socket adapter for rotation with respect to the base plate subassembly.

In a fourth statement of the coupling-socket adapter assembly of the invention, the coupling-socket adapter assembly is for a prosthetic limb and includes a base plate subassembly, a coupling-socket adapter, and an adjustable-diameter ring-clamp. The base plate subassembly is attachable to a first prosthetic limb component. The coupling-socket adapter is rotatably attached to the base plate subassembly, has an upper portion and a lower portion, and has a cavity for receiving a male coupling member (such as a boss of a pyramidal link-plate). The lower portion includes a tapered outside circumferential surface. The ring-clamp is positioned between the base plate subassembly and the upper portion of the coupling-socket adapter and has a tapered inside circumferential surface which surrounds the tapered outside circumferential surface of the lower portion of the coupling-socket adapter. Decreasing the diameter of the ring clamp locks the coupling-socket adapter against rotation with respect to the base plate subassembly, and increasing the diameter of the ring-clamp unlocks the coupling-socket adapter for rotation with respect to the coupling-socket adapter.

In a fifth statement of the coupling-socket adapter assembly of the invention, the coupling-socket adapter assembly is for a prosthetic limb and includes a base plate subassembly, a coupling-socket adapter, a threaded fastener, and a rotational locking and unlocking mechanism. The base plate subassembly is attachable to a first prosthetic limb component and includes a tapered hole having a longitudinal axis and a tapered side wall. The coupling-socket adapter has a cavity for receiving a male coupling member (such as a boss of a pyramidal link-plate). The threaded fastener has a tapered portion positioned in the tapered hole and is threadably attached to the coupling-socket adapter so that the coupling-socket adapter is rotatably attached to the base plate subassembly. The mechanism longitudinally moves the threaded fastener, in a first direction, into frictional-locking engagement with the tapered side wall for locking the coupling-socket adapter against rotation with respect to the base plate subassembly. The mechanism moves the threaded fastener, in a direction opposite to the first direction, out of frictional-locking engagement with the tapered side wall for unlocking the coupling-socket adapter for rotation with respect to the base plate subassembly. The mechanism is operably when the base plate subassembly is attached to the first prosthetic limb component.

In a sixth statement of the coupling-socket adapter assembly of the invention, the coupling-socket adapter assembly is for a prosthetic limb and includes a base plate subassembly, a coupling-socket adapter, and a threaded press. The base plate subassembly is attachable to a first prosthetic limb component. The coupling-socket adapter is positioned adjacent to the base plate subassembly. One of the base plate subassembly and the coupling-socket adapter includes a conical cavity that widens with the distance from the other one of the base plate subassembly and the coupling-socket adapter. The other one of the base plate subassembly and the coupling-socket adapter includes a conical projection extending therefrom and into the conical cavity, the conical projection widens with the distance from the other one of the base plate subassembly and the coupling-socket adapter. The threaded press is operative to push the base plate subassembly away from the coupling-socket adapter, thereby causing the conical projection to frictionally lock against the inner surface of the conical cavity, whereby the coupling-socket adapter is rotatable with respect to the base plate subassembly when the threaded press is deactivated, but is rotationally locked with respect to the base plate subassembly when the threaded press is activated.

Preferably, for each coupling-socket adapter assembly described in the previous six paragraphs, the base plate subassembly includes a base plate, a slide plate, and a slide locking and unlocking device. The base plate is attachable to the first prosthetic limb component and has a rectilinear surface groove. The slide plate is slidably captured in the surface groove, and the coupling-socket adapter is rotatable attached to the slide plate. The device locks the slide plate against sliding in the surface groove and unlocks the slide plate for sliding in the surface groove. The device is operable when the base plate is attached to the first prosthetic limb component.

Several benefits and advantages are derived from the invention. Rotatably attaching a coupling-socket adapter to a base plate subassembly and providing a mechanism, such as the previously-described ring or ring-clamp, allows rotatable adjustment, including infinite rotational adjustments, for the prosthetic limb while the coupling-socket adapter assembly remains attached to the first prosthetic limb component. The ring does not significantly increase the profile or height of the attachment of the interconnection components. When present, the optional slide plate and optional slide locking and unlocking device of the base plate subassembly allow translational adjustment, including infinite translational adjustment, along a linear axis between two end positions for the prosthetic limb while the coupling-socket adapter assembly remains attached to the first prosthetic limb component.

BRIEF DESCRIPTION OF THE DRAWINGS

FIG. 1b is a partially-exploded, side-elevational view of a prior-art prosthetic limb (described above) utilizing the prior-art pyramidal link-plate of FIG. 1a;

DETAILED DESCRIPTION

Figure 1B:
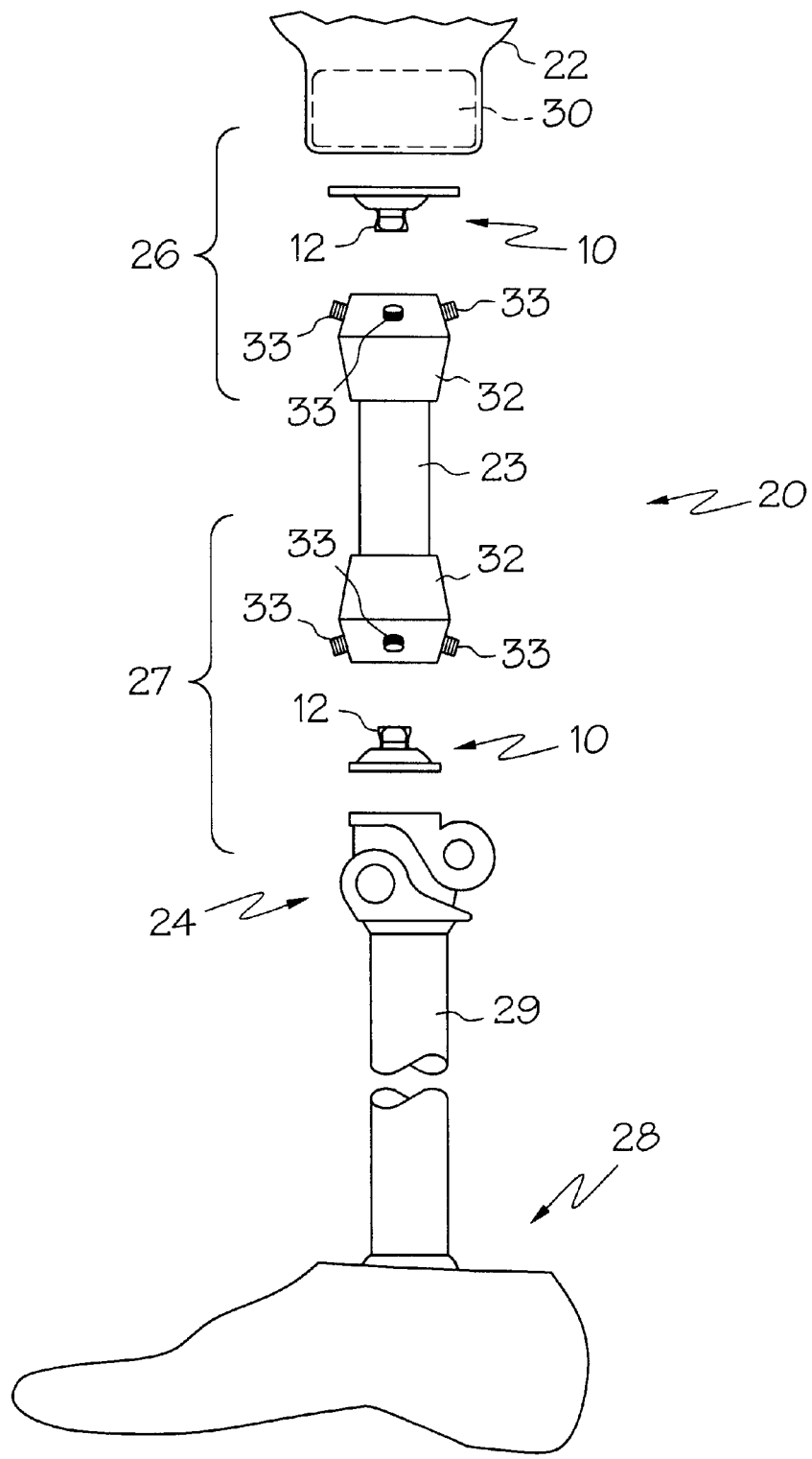
Figure 2:
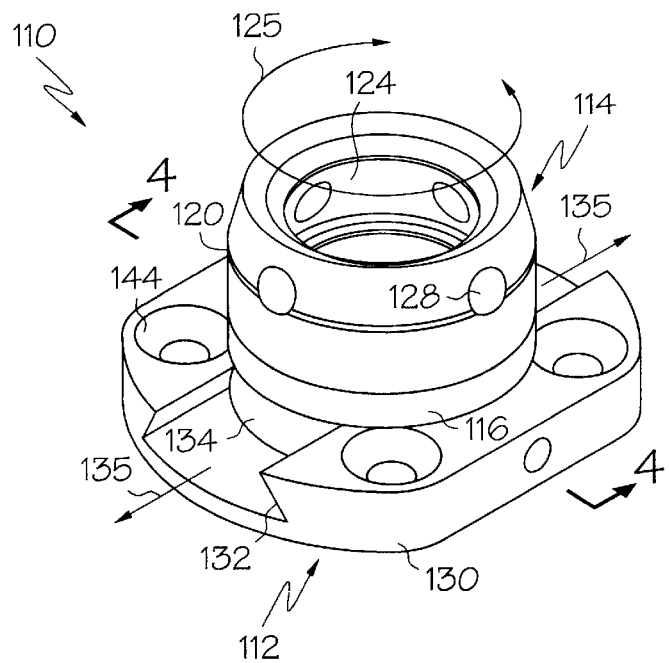
FIG. 2 is a perspective, schematic view of a first preferred embodiment of the coupling-socket adapter assembly of the invention.
Figure 3:
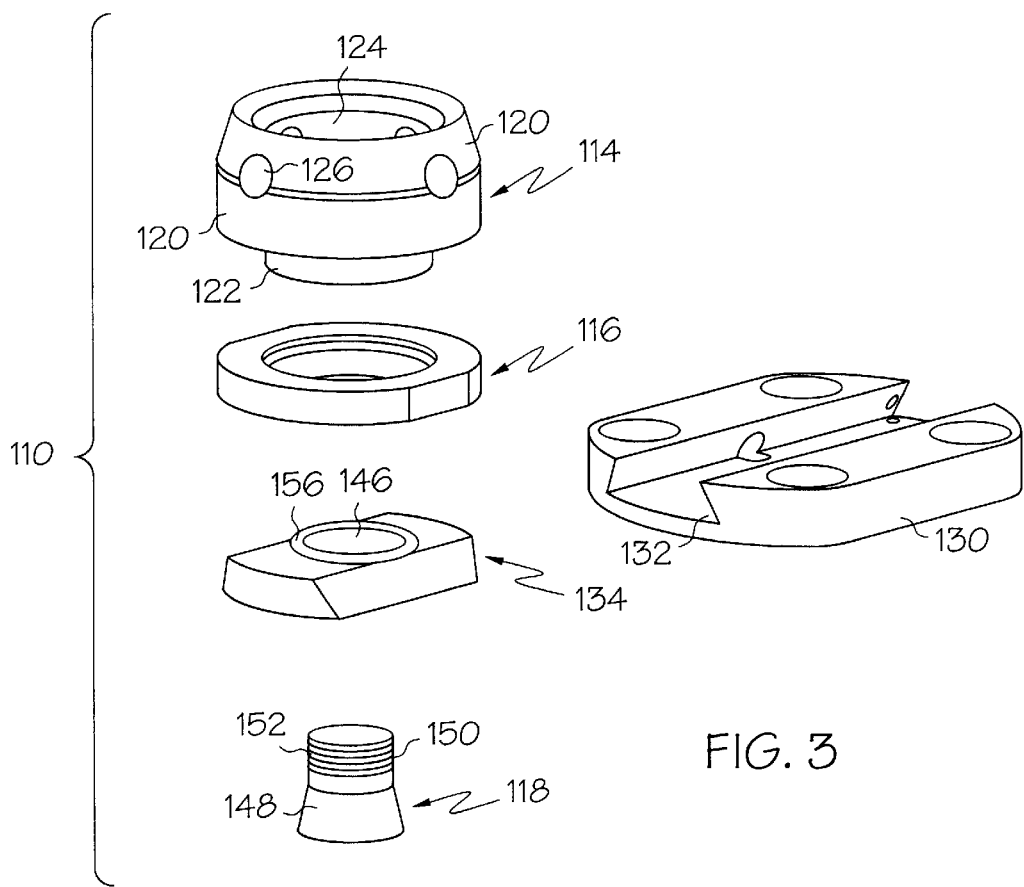
FIG. 3 is an exploded view of the coupling-socket adapter assembly of FIG. 2.
Figure 4:
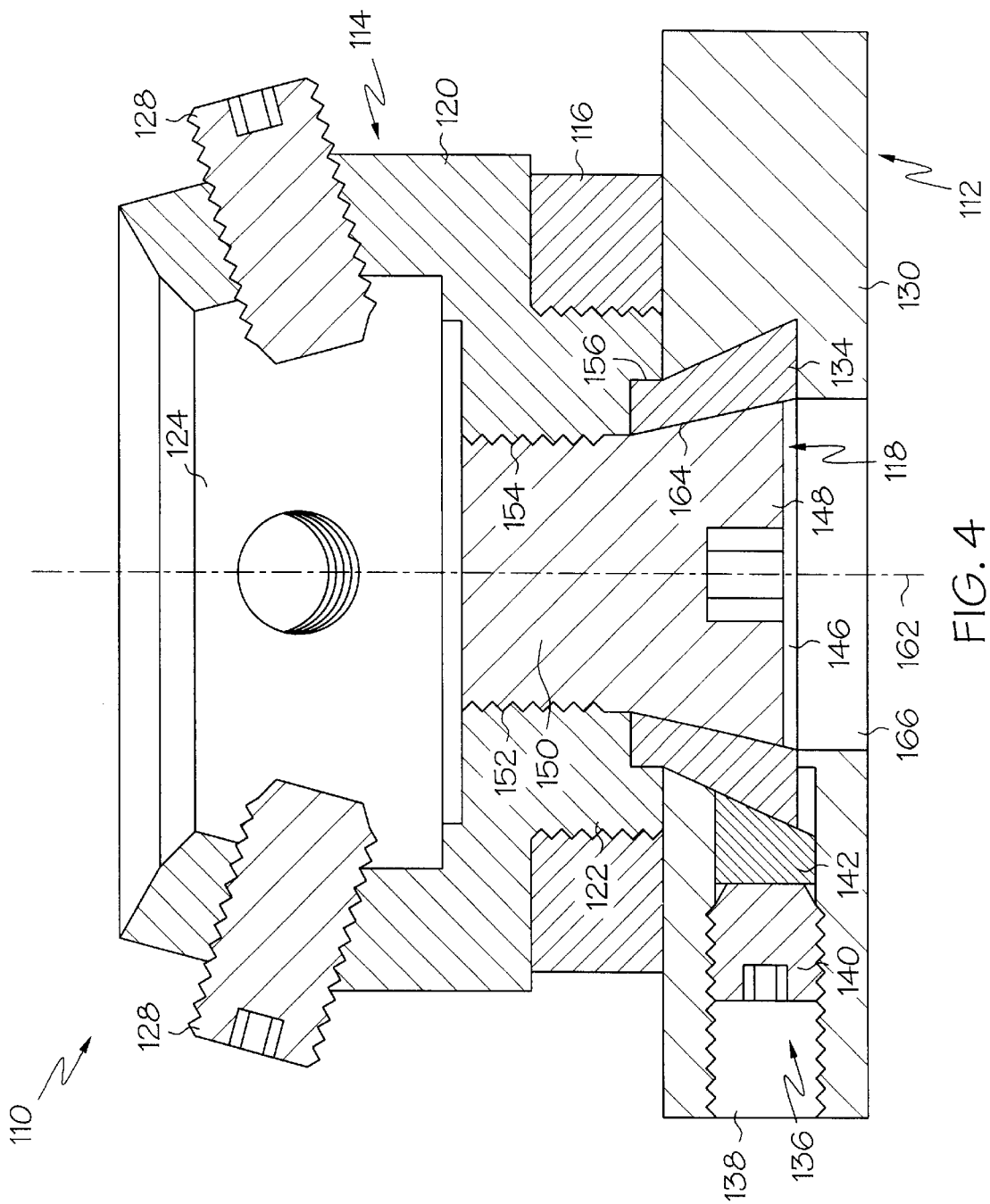
FIG. 4 is a cross-sectional view of the coupling-socket adapter assembly of FIG. 2, taken along lines 4—4 in FIG. 2, which also includes set screws.

A first preferred embodiment of the coupling-socket adapter assembly 110 of the invention is shown in FIGS. 2–4. The coupling-socket adapter assembly 110 is for a prosthetic limb 20 shown in FIG. 1b. The coupling-socket adapter assembly 110 includes a base plate subassembly 112, a coupling-socket adapter 114, a ring 116, and a threaded fastener 118. The base plate subassembly 112 is attachable to a first prosthetic limb component such as, without limitation, the knee joint assembly 24 or the locking assembly 30 shown in FIG. 1b.

Figure 1A:
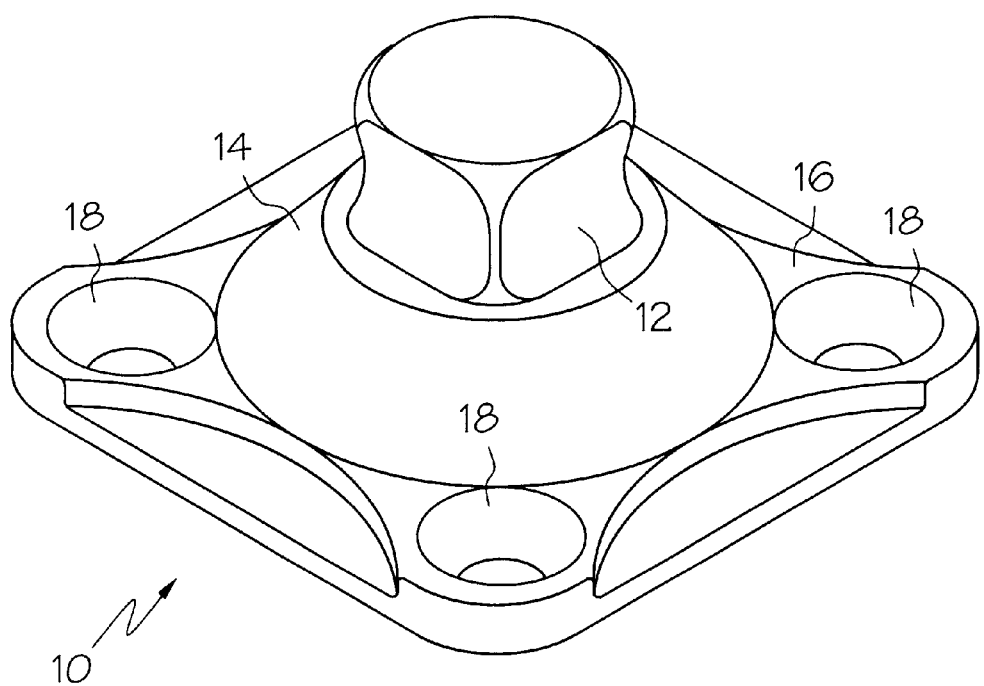
FIG. 1a is a perspective view of a prior-art pyramidal link-plate (described above)

The coupling-socket adapter 114 is rotatably attached to the base plate subassembly 112, has an upper portion 120 and a lower portion 122, and has a cavity 124 for receiving a male coupling member such as, without limitation, a boss 12 of a pyramidal link-plate 10 shown in FIGS. 1a and 1b. The rotational adjustability provided by the coupling-socket adapter assembly 110 is indicated by a double-headed arrow 125 in FIG. 2. The coupling-socket adapter 114 includes a plurality of internally-threaded holes 126 having an outside end disposed in the upper portion 120 of the coupling-socket adapter 114 and having an inside end in communication with the cavity 124 of the coupling-socket adapter 114. The coupling-socket adapter assembly 110 includes a plurality of set screws 128 threadably disposed in a corresponding internally-threaded hole 126 of the coupling-socket adapter 114. The internally-threaded holes 126 of the coupling-socket adapter 114 are angled towards the lower portion 122 of the coupling-socket adapter 114 as one moves inward in the internally-threaded holes 126 of the coupling-socket adapter 114 towards the cavity 124 of the coupling-socket adapter 114.

The ring 116 surrounds, and is threadably attached to, the lower portion 122 of the coupling-socket adapter 114, and is disposed between the base plate subassembly 112 and the upper portion 120 of the coupling-socket adapter 114. As will be explained later, rotation of the ring 116 with respect to the coupling-socket adapter 114 locks the coupling-socket adapter 114 against rotation with respect to the base plate subassembly 112. Likewise, counterrotation of the ring 116 with respect to the coupling-socket adapter 114 unlocks the coupling socket adapter 114 for rotation with respect to the base plate subassembly 112.

The base plate subassembly 112 includes a base plate 130 which is attachable to the first prosthetic limb component and which has a rectilinear surface groove 132. The base plate subassembly 112 also includes a slide plate 134 slidably captured in the surface groove 132, wherein the coupling-socket adapter 114 is rotatably attached to the slide plate 134, and wherein the ring 116 is disposed between the base plate 130 and the upper portion 120 of the coupling-socket adapter 114. The slidable adjustment ability provided by the slide plate 134 is indicated by two arrows 135 in FIG. 2. It is noted that there is play between the ring 116 and the base plate 130 for the rotationally-locked coupling-socket adapter and for the rotationally-unlocked coupling-socket adapter. Preferably, the surface groove 132 is a dovetail-shaped surface groove, and the slide plate 134 is a dovetail-shaped slide plate. The base plate subassembly 112 further includes means 136 for locking the slide plate 134 against sliding in the surface groove 132 and for unlocking the slide plate 134 for sliding in the surface groove 132, wherein the slide-plate locking and unlocking means 136 is operable when the base plate 130 is attached to the first prosthetic limb component. Preferably such means 136 includes the base plate 130 having an internally-threaded hole 138, a set screw 140 disposed in the internally-threaded hole 138 of the base plate 130, and a slidable member 142 pushed by the set screw 140 and having an angled surface to engage and lock the slide plate 134. The base plate 130 includes a plurality of countersunk holes 144 for bolted attachment of the base plate 130 to the first prosthetic limb component.

The slide plate 134 (and hence the base plate subassembly 112) includes a tapered hole 146, and the threaded fastener 118 is threadably attached to the coupling-socket adapter 114 and has a tapered portion 148 disposed in the tapered hole 146. The threaded fastener 118 includes a cylindrical portion 150 extending from the tapered portion 148 and having external threads 152. The coupling-socket adapter 114 has internal threads 154, and the external threads 152 of the cylindrical portion 150 are threadably engaged with the internal threads 154 of the coupling-socket adapter 114. The slide plate 134 has an annular boss 156, and the boss 156 has a top surface and a circumferential side surface. The lower portion 122 of the coupling-socket adapter 114 surrounds the top and circumferential side surfaces of the boss 156. The cylindrical portion 150 of the threaded fastener 118 is in communication with the cavity 124 of the coupling-socket adapter 114. The cavity 124 of the coupling-socket adapter 114 is disposed entirely within the upper portion 120 of the coupling-socket adapter 114.

In operation, the base plate subassembly 112 is attached to the first prosthetic limb component. A second prosthetic limb component is obtained which has an attached prosthetic-limb link-member (such as a pyramidal link-plate). The boss of the prosthetic-limb link-member is secured in the cavity 124 of the coupling-socket adapter 114 using the set screws 128. The second prosthetic limb component is rotated to a desired position with respect to the first prosthetic limb component. Then, the ring 116 is rotated, with respect to the coupling-socket adapter 114, in a first direction, to increase the gap between the ring 116 and the upper portion 120 of the coupling-socket adapter 114 which pulls the threaded fastener 118 so that its tapered portion 148 is brought into frictional-locking engagement with the tapered side wall 164 of the tapered hole 146 of the slide plate 134 thereby locking the coupling-socket adapter 114 against rotation with respect to the base plate subassembly 112. To change the angle between the first and the second prosthetic limb components, the ring 116 is counterrotated, with respect to the coupling-socket adapter 114, in a direction opposite to the first direction, to decrease the gap between the ring 116 and the upper portion 120 of the coupling-socket adapter 114 which releases the pull on the threaded fastener 118 so that its tapered portion 148 is brought out of frictional-locking engagement with the tapered side wall 164 of the tapered hole 146 of the slide plate 134 thereby unlocking the coupling-socket adapter 114 for rotation with respect to the base plate subassembly 112. The required change in the gap size between the ring 116 and the upper portion 120 for rotational locking and unlocking is very small, as can be appreciated by the artisan. Before, with, or after the rotational adjustment, the slide plate 134 is slid in the surface groove 132 to a desired position and locked in place by the set screw 140.

Figure 5:
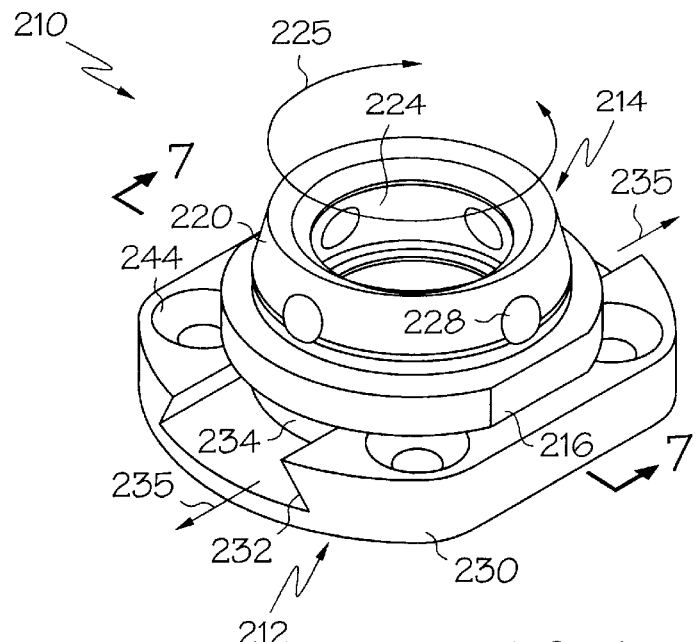
FIG. 5 is a perspective, schematic view of a second preferred embodiment of the coupling-socket adapter assembly of the invention.
Figure 6:
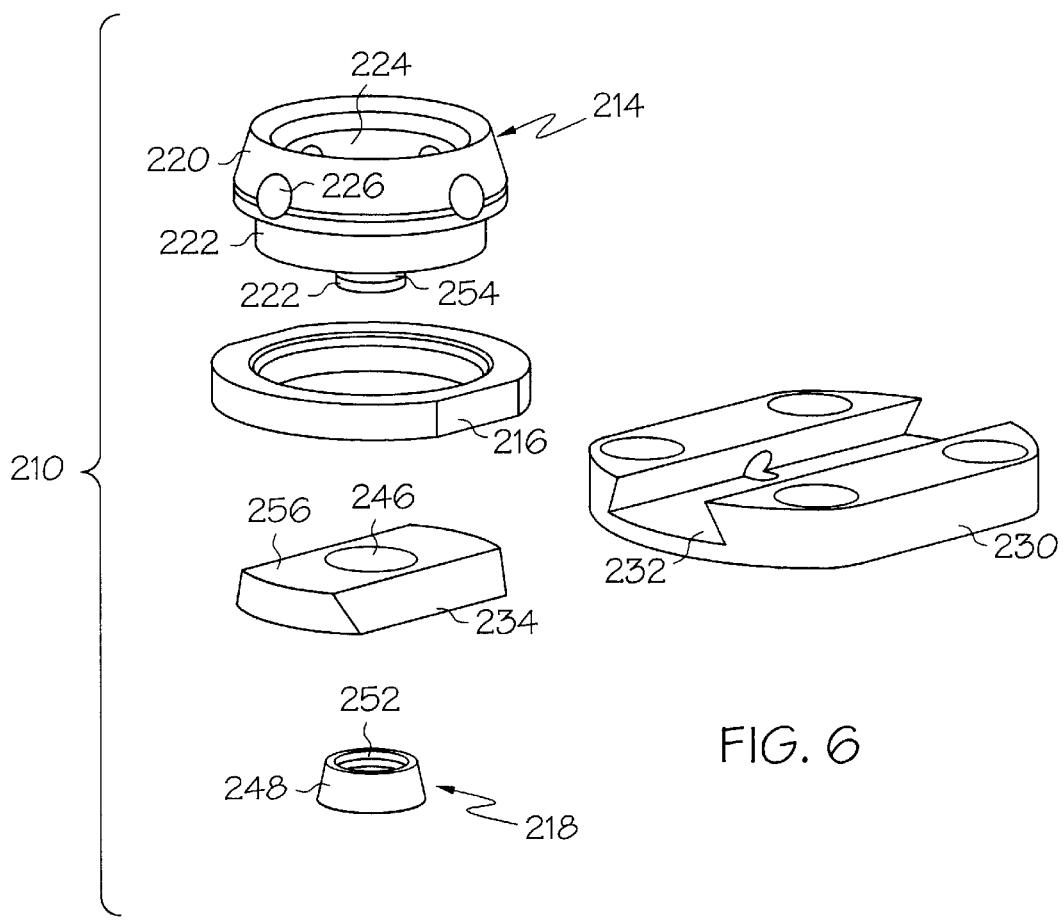
FIG. 6 is an exploded view of the coupling-socket adapter assembly of FIG. 5.
Figure 7:
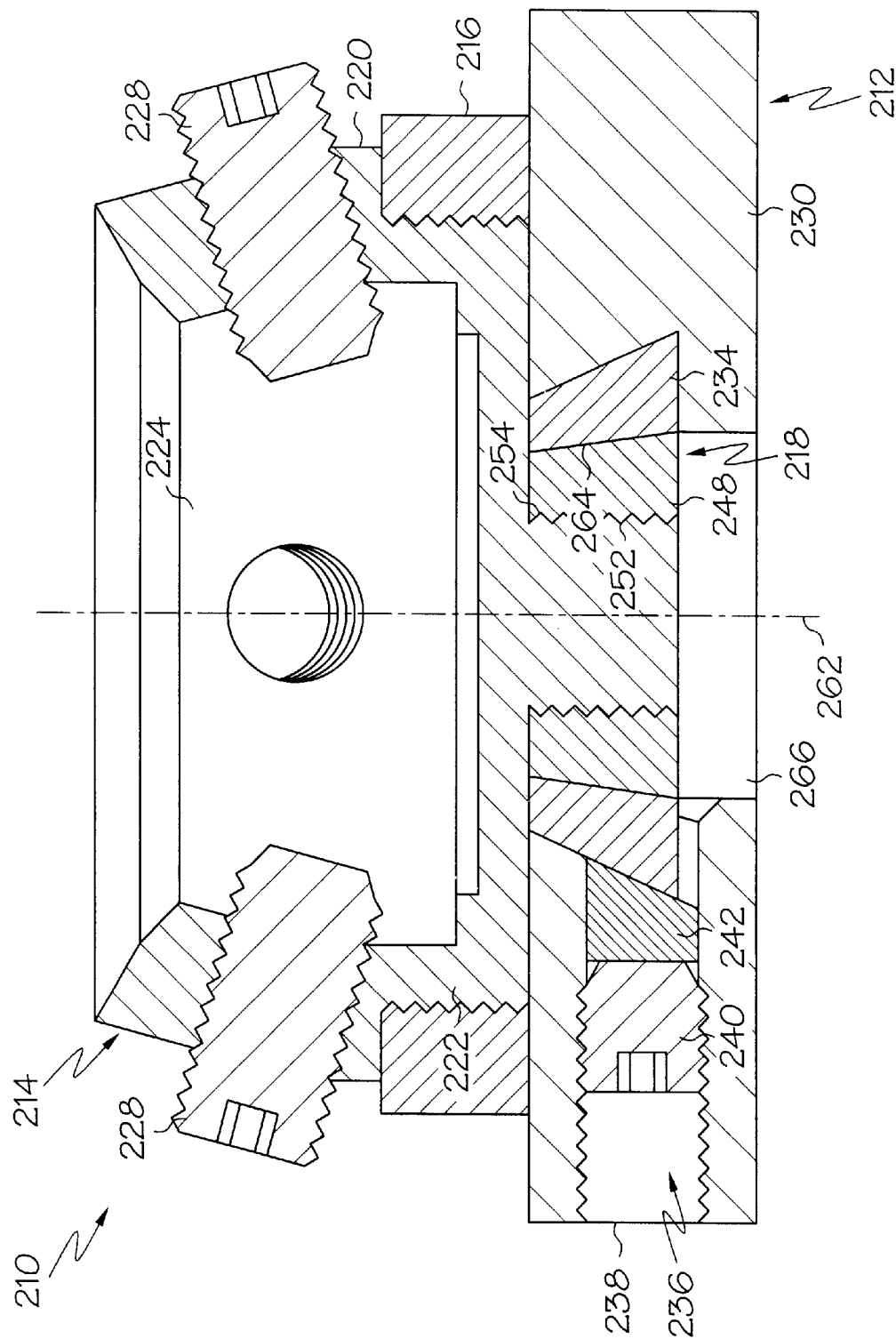
FIG. 7 is a cross-sectional view of the coupling-socket adapter assembly of FIG. 5, taken along lines 7—7 in FIG. 5, which also includes set screws.

A second preferred embodiment of the coupling-socket adapter assembly 210 of the invention is shown in FIGS. 5–7. The coupling-socket adapter assembly 210 is for a prosthetic limb 20 shown in FIG. 1b. The coupling-socket adapter assembly 210 includes a base plate subassembly 212, a coupling-socket adapter 214, a ring 216, and a threaded fastener 218. The base plate subassembly 212 is attachable to a first prosthetic limb component such as, without limitation, the knee joint assembly 24 or the locking assembly 30 shown in FIG. 1b.

The coupling-socket adapter 214 is rotatably attached to the base plate subassembly 212, has an upper portion 220 and a lower portion 222, and has a cavity 224 for receiving a male coupling member such as, without limitation, a boss 12 of a pyramidal link-plate 10 shown in FIGS. 1a and 1b. The rotational adjustability provided by the coupling-socket adapter assembly 210 is indicated by a double-headed arrow 225 in FIG. 5. The coupling-socket adapter 214 includes a plurality of internally-threaded holes 226 having an outside end disposed in the upper portion 220 of the coupling-socket adapter 214 and having an inside end in communication with the cavity 224 of the coupling-socket adapter 214. The socket adapter assembly 210 includes a plurality of set screws 228 threadably disposed in a corresponding internally-threaded hole 226 of the coupling-socket adapter 214. The internally-threaded holes 226 of the coupling-socket adapter 214 are angled towards the lower portion 222 of the coupling-socket adapter 214 as one moves inward in the internally-threaded holes 226 of the coupling-socket adapter 214 towards the cavity 224 of the coupling-socket adapter 214.

The ring 216 surrounds, and is threadably attached to, the lower portion 222 of the coupling-socket adapter 214, and is disposed between the base plate subassembly 212 and the upper portion 220 of the coupling-socket adapter 214. As will be explained later, rotation of the ring 216 with respect to the coupling-socket adapter 214 locks the coupling-socket adapter 214 against rotation with respect to the base plate subassembly 212. Likewise, counterrotation of the ring 216 with respect to the coupling-socket adapter 214 unlocks the coupling socket adapter 214 for rotation with respect to the base plate subassembly 212.

The base plate subassembly 212 includes a base plate 230 which is attachable to the first prosthetic limb component and which has a rectilinear surface groove 232. The base plate subassembly 212 also includes a slide plate 234 slidably captured in the surface groove 232, wherein the coupling-socket adapter 214 is rotatably attached to the slide plate 234, and wherein the ring 216 is disposed between the base plate 230 and the upper portion 220 of the coupling-socket adapter 214. The slidable adjustment ability provided by the slide plate 234 is indicated by two arrows 235 in FIG. 5. It is noted that there is play between the ring 216 and the base plate 230 for the rotationally-locked coupling-socket adapter and for the rotationally-unlocked coupling-socket adapter. Preferably, the surface groove 232 is a dovetail-shaped surface groove, and the slide plate 234 is a dovetail-shaped slide plate. The base plate subassembly 212 further includes means 236 for locking the slide plate 234 against sliding in the surface groove 232 and for unlocking the slide plate 234 for sliding in the surface groove 232, wherein the slide-plate locking and unlocking means 236 is operable when the base plate 230 is attached to the first prosthetic limb component. Preferably such means 236 includes the base plate 230 having an internally-threaded hole 238, a set screw 240 disposed in the internally-threaded hole 238 of the base plate 230, and a slidable member 242 pushed by the set screw 240 and having an angled surface to engage and lock the slide plate 234. The base plate 230 includes a plurality of countersunk holes 244 for bolted attachment of the base plate 230 to the first prosthetic limb component.

The slide plate 234 (and hence the base plate subassembly 212) includes a tapered hole 246, and the threaded fastener 218 is threadably attached to the coupling-socket adapter 214 and has a tapered portion 248 disposed in the tapered hole 246. The tapered portion 248 has internal threads 252. The lower portion 222 of the coupling-socket adapter 214 has external threads 254, and the internal threads 252 of the tapered portion 248 are threadably engaged with the external threads 254 of the lower portion 222. The tapered portion 248 is an entire portion of the threaded fastener 218. The slide plate 234 has a top surface 256, wherein the top surface 256 is a substantially planar surface. The cavity 224 of the coupling-socket adapter 214 is disposed partially in the upper portion 220 of the coupling-socket adapter 214 and partially in the lower portion 222 of the coupling-socket adapter 214.

The operation of the coupling-socket adapter assembly 210 of the second preferred embodiment of the invention is identical to the previously-described operation of the coupling-socket adapter assembly 110 of the first preferred embodiment of the invention.

The previously-described first and second preferred embodiments can be collectively described, in a first broad expression of the invention, as a coupling-socket adapter assembly 110 and 210, for a prosthetic limb, which includes a base plate subassembly 112 and 212, a coupling-socket adapter 114 and 214, and a ring 116 and 216. The base plate subassembly 112 and 212 is attachable to a first prosthetic limb component. The coupling-socket adapter 114 and 214 is rotatably attached to the base plate subassembly 112 and 212, has an upper portion 120 and 220 and a lower portion 122 and 222, and has a cavity 124 and 224 for receiving a male coupling member. The ring 116 and 216 surrounds the lower portion 122 and 222 of the coupling-socket adapter 114 and 214, is disposed between the base plate subassembly 112 and 212 and the upper portion 120 and 220 of the coupling-socket adapter 114 and 214, and is threadably engaged with at least one of the base plate subassembly 112 and 212 and the coupling-socket adapter 114 and 214. Rotation of the ring with respect to at least one of the base plate subassembly and the coupling-socket adapter locks the coupling-socket adapter against rotation with respect to the base plate subassembly, and counterrotation of the ring with respect to at least one of the base plate subassembly and the coupling-socket adapter unlocks the coupling-socket adapter for rotation with respect to the base plate subassembly.

In the first broad expression of the invention, the base plate subassembly may include a base plate and a slide plate, as previously described, or may include a slide plate which slides in a surface groove of the first prosthetic limb component, or may lack a slide plate and have the tapered hole in the base plate, etc. Also, the coupling-socket adapter may be rotatably attached to the base plate subassembly by using a threaded fastener, as previously described, or by using any other rotational attachment, as is within the level of skill of the artisan. When a threaded fastener is used, it need not have a tapered portion as long as it is not capable of passing completely through the hole of the base plate subassembly. It is noted that when a base plate and a slide plate are present, the ring must bottom out on the slide plate and not on the base plate to maintain independence of the rotational and sliding features, as can be appreciated by the artisan. As can be understood by those skilled in the art, the rotational locking and unlocking property of the ring can also be achieved by replacing (or supplementing) the threads of the coupling-socket adapter with threads on the base plate subassembly.

Figure 8:
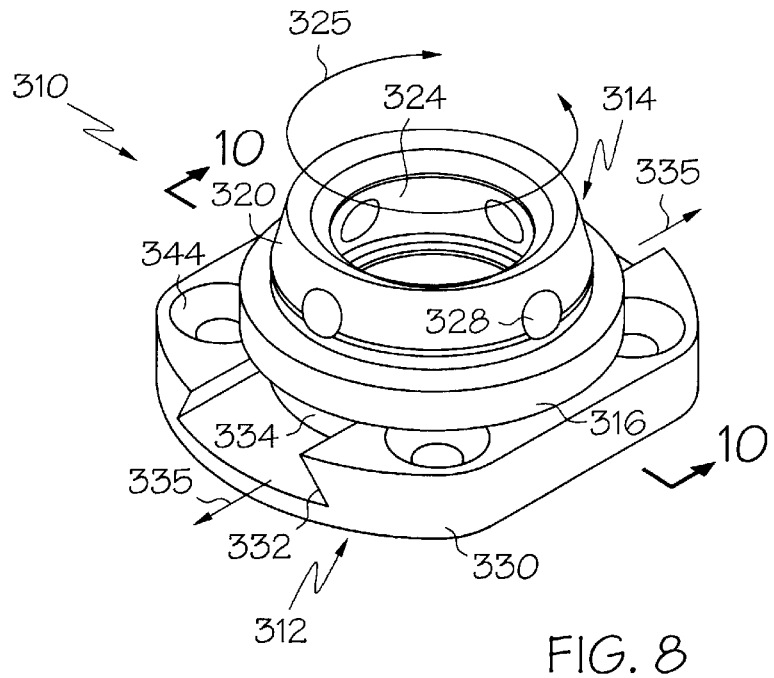
FIG. 8 is a perspective, schematic view of a third preferred embodiment of the coupling-socket adapter assembly of the invention.
Figure 9:
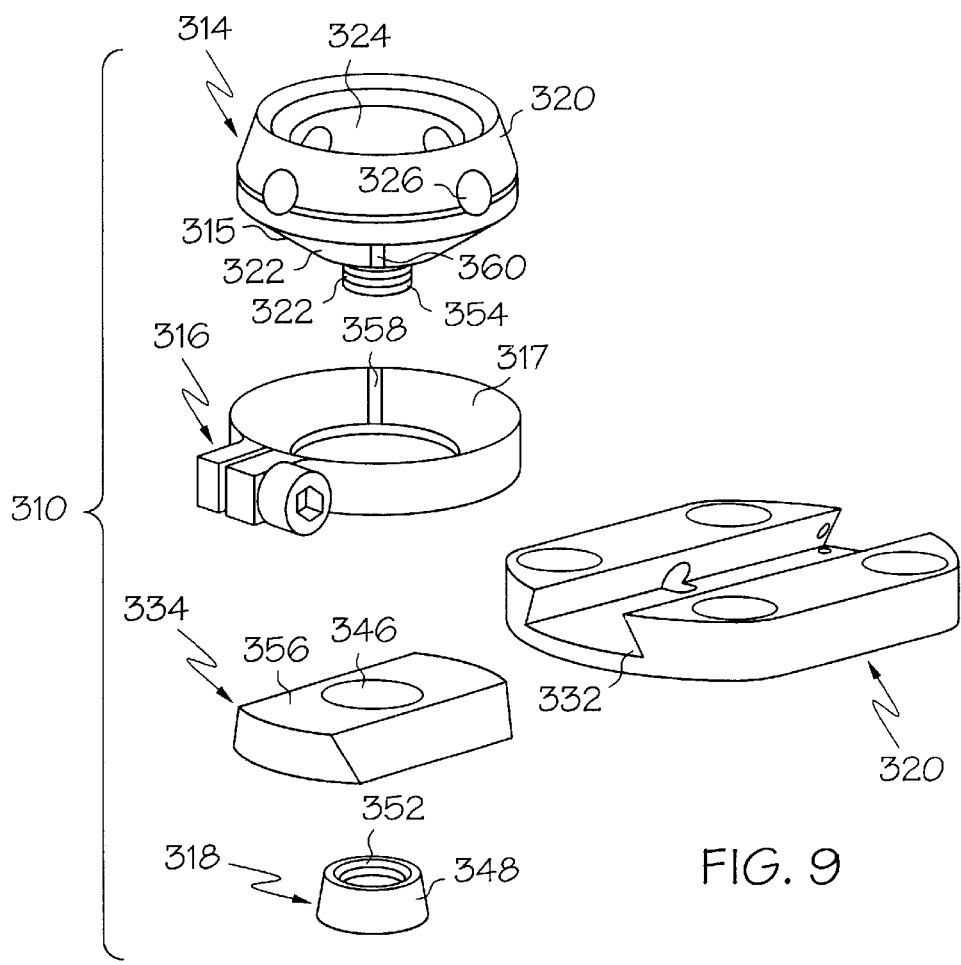
FIG. 9 is an exploded view of the coupling-socket adapter assembly of FIG. 8 with the ring-clamp turned 180 degrees from its orientation in FIG. 8.
Figure 10:
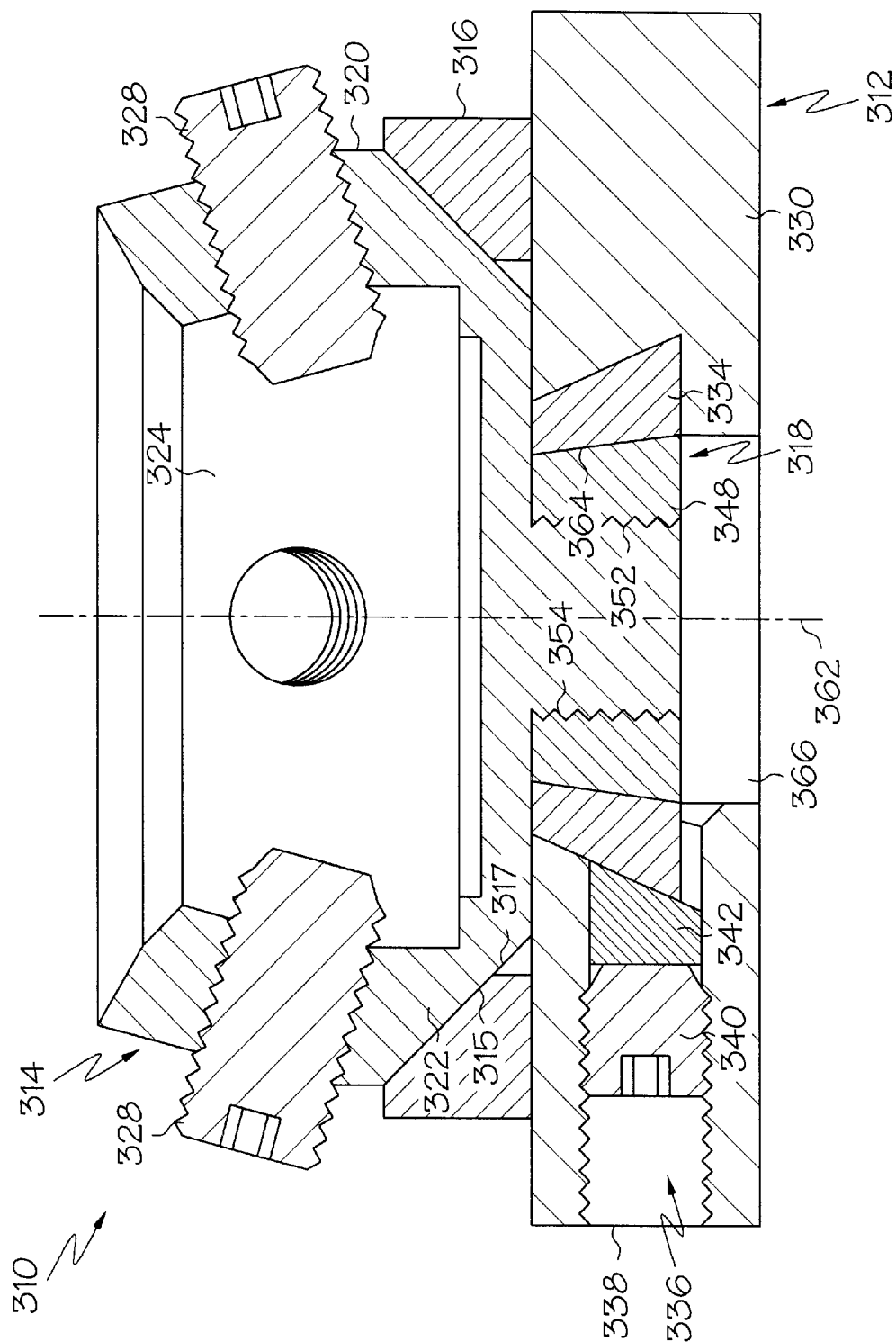
FIG. 10 is a cross-sectional view of the coupling-socket adapter assembly of FIG. 8, taken along lines 10—10 in FIG. 8, which also includes set screws and with the ring-clamp turned 90 degrees from its orientation in FIG. 8.

A third preferred embodiment of the coupling-socket adapter assembly 310 of the invention is shown in FIGS. 8–10. The coupling-socket adapter assembly 310 is for a prosthetic limb 20 shown in FIG. 1b. The coupling-socket adapter assembly 310 includes a base plate subassembly 312, a coupling-socket adapter 314, an adjustable-diameter ring-clamp 316, and a threaded fastener 318. The base plate subassembly 312 is attachable to a first prosthetic limb component such as, without limitation, the knee joint assembly 24 or the locking assembly 30 shown in FIG. 1b.

The coupling-socket adapter 314 is rotatably attached to the base plate subassembly 312, has an upper portion 320 and a lower portion 322, and has a cavity 124 for receiving a male coupling member such as, without limitation, a boss 12 of a pyramidal link-plate 10 shown in FIGS. 1a and 1b. The rotational adjustability provided by the coupling-socket adapter assembly 310 is indicated by a double-headed arrow 325 in FIG. 8. The lower portion 322 of the coupling-socket adapter 314 includes a tapered outside circumferential surface 315. The coupling-socket adapter 314 includes a plurality of internally-threaded holes 326 having an outside end disposed in the upper portion 320 of the coupling-socket adapter 314 and having an inside end in communication with the cavity 324 of the coupling-socket adapter 314. The coupling-socket adapter assembly 310 includes a plurality of set screws 328 threadably disposed in a corresponding internally-threaded hole 326 of the coupling-socket adapter 314. The internally-threaded holes 326 of the coupling-socket adapter 314 are angled towards the lower portion 322 of the coupling-socket adapter 314 as one moves inward in the internally-threaded holes 326 of the coupling-socket adapter 314 towards the cavity 324 of the coupling-socket adapter 314.

The ring-clamp 316 is disposed between the base plate subassembly 312 and the upper portion 320 of the coupling-socket adapter 314 and has a tapered inside circumferential surface 317 which surrounds the tapered outside circumferential surface 315 of the lower portion 322 of the coupling-socket adapter 314. As will be explained later, decreasing the diameter of the ring-clamp 316 locks the coupling-socket adapter 314 against rotation with respect to the base plate subassembly 312. Likewise, increasing the diameter of the ring-clamp 316 unlocks the coupling socket adapter 314 for rotation with respect to the base plate subassembly 312. The ring-clamp 316 and the coupling-socket adapter 314 are keyed to prevent rotation relative to each other such as by the tapered inside circumferential surface 317 of the ring-clamp 316 having a longitudinally extending rib 358 and the tapered outside circumferential surface 315 of the lower portion 322 of the coupling-socket adapter 314 having a corresponding longitudinally extending channel 360.

The base plate subassembly 312 includes a base plate 330 which is attachable to the first prosthetic limb component and which has a rectilinear surface groove 332. The base plate subassembly 312 also includes a slide plate 334 slidably captured in the surface groove 332, wherein the coupling-socket adapter 314 is rotatably attached to the slide plate 334, and wherein the ring-clamp 316 is disposed between the base plate 330 and the upper portion 320 of the coupling-socket adapter 314. The slidable adjustment ability provided by the slide plate 334 is indicated by two arrows 335 in FIG. 8. It is noted that there is play between the ring-clamp 316 and the base plate 330 for the rotationally-locked coupling-socket adapter and for the rotationally-unlocked coupling-socket adapter. Preferably, the surface groove 332 is a dovetail-shaped surface groove, and the slide plate 334 is a dovetail-shaped slide plate. The base plate subassembly 312 further includes means 336 for locking the slide plate 334 against sliding in the surface groove 332 and for unlocking the slide plate 334 for sliding in the surface groove 332, wherein the slide-plate locking and unlocking means 336 is operable when the base plate 330 is attached to the first prosthetic limb component. Preferably such means 336 includes the base plate 330 having an internally-threaded hole 338, a set screw 340 disposed in the internally-threaded hole 338 of the base plate 330, and a slidable member 342 pushed by the set screw 340 and having an angled surface to engage and lock the slide plate 334. The base plate 330 includes a plurality of countersunk holes 344 for bolted attachment of the base plate 330 to the first prosthetic limb component.

The slide plate 334 (and hence the base plate subassembly 312) includes a tapered hole 346, and the threaded fastener 318 is threadably attached to the coupling-socket adapter 314 and has a tapered portion 348 disposed in the tapered hole 346. The tapered portion 348 has internal threads 352. The lower portion 322 of the coupling-socket adapter 314 has external threads 354, and the internal threads 352 of the tapered portion 348 are threadably engaged with the external threads 354 of the lower portion 322 of the coupling-socket adapter 314. The tapered portion 348 is an entire portion of the threaded fastener 318. The slide plate 334 has a top surface 356, wherein the top surface 356 is a substantially planar surface. The cavity 324 of the coupling-socket adapter 314 is disposed partially in the upper portion 320 of the coupling-socket adapter 314 and partially in the lower portion 322 of the coupling-socket adapter 314.

In operation, the base plate subassembly 312 is attached to the first prosthetic limb component. A second prosthetic limb component is obtained which has an attached prosthetic-limb link- member (such as a pyramidal link-plate). The boss of the prosthetic-limb link-member is secured in the cavity 324 of the coupling-socket adapter 314 using the set screws 328. The second prosthetic limb component is rotated to a desired position with respect to the first prosthetic limb component. Then, the ring-clamp 316 is tightened to decrease its diameter which causes the tapered outside circumferential surface 315 of the lower portion 322 of the coupling-socket adapter 314 to longitudinally slide, with respect to the tapered inside circumferential surface 317 of the ring-clamp 316, in a first direction which pulls the threaded fastener 318 so that its tapered portion 348 is brought into frictional-locking engagement with the tapered side wall 364 of the tapered hole 346 of the slide plate 334 thereby locking the coupling-socket adapter 314 against rotation with respect to the base plate subassembly 312. To change the angle between the first and the second prosthetic limb components, the ring-clamp 316 is loosened to increase its diameter which releases the pull on the threaded fastener 318 so that its tapered portion 348 is brought out of frictional-locking engagement with the tapered side wall 364 of the tapered hole 346 of the slide plate 334 thereby unlocking the coupling -socket adapter 314 for rotation with respect to the base plate subassembly 312. The longitudinal component of the required slide distance for rotational locking and unlocking is very small, as can be appreciated by the artisan. Before, with, or after the rotational adjustment, the slide plate 334 is slid in the surface groove 332 to a desired position and locked in place by the set screw 340.

The previously-described first, second, and third preferred embodiments can be collectively described, in a second broad expression of the invention, as a coupling-socket adapter assembly 110, 210, and 310, for a prosthetic limb, which includes a base plate subassembly 112, 212, and 312, a coupling-socket adapter 114, 214, and 314, and a threaded fastener 118, 218, and 318. The base plate subassembly is attachable to a first prosthetic limb component and includes a tapered hole 146, 246, and 346 having a longitudinal axis 162, 262, and 362 and a tapered side wall 164, 264, and 364. The coupling-socket adapter has a cavity 124, 224, and 324 for receiving a male coupling member. The threaded fastener has a tapered portion 148, 248, and 348 which is disposed in the tapered hole and which is threadably attached to the coupling-socket adapter so that the coupling-socket adapter is rotatably attached to the base plate subassembly. The coupling-socket adapter assembly also includes means for longitudinally moving the threaded fastener, in a first direction, into frictional-locking engagement with the tapered side wall for locking the coupling-socket adapter against rotation with respect to the base plate subassembly and for longitudinally moving the threaded fastener, in a direction opposite to the first direction, out of frictional-locking engagement with the tapered side wall for unlocking the coupling-socket adapter for rotation with respect to the base plate subassembly. Preferably, such longitudinal moving means includes the previously-described rings 116 and 216 and/or the previously-described ring-clamp 316, and the like.

In the second broad expression of the invention, the base plate subassembly may include a base plate and a slide plate, as previously described, or may include a slide plate which slides in a surface groove of the first prosthetic limb component, or may lack a slide plate and have the tapered hole in the base plate, etc. Also, the coupling-socket adapter may be rotatably attached to the base plate subassembly by using a threaded fastener, as previously described, or by using any other rotational attachment, as is within the level of skill of the artisan. When a threaded fastener is used, it need not have a tapered portion as long as it is not capable of passing completely through the hole of the base plate subassembly. It is noted that when a base plate and a slide plate are present, the ring must bottom out on the slide plate and not on the base plate to maintain independence of the rotational and sliding features, as can be appreciated by the artisan. As can be understood by those skilled in the art, the rotational locking and unlocking property of the ring can also be achieved by replacing (or supplementing) the threads of the coupling-socket adapter with threads on the base plate subassembly.

Alternatively, the previously-described first, second, and third preferred embodiments can be collectively described, in a third broad expression of the invention, as a coupling-socket adapter assembly 110, 210, and 310, for a prosthetic limb, which includes a base plate subassembly 112, 212, and 312, a coupling-socket adapter 114, 214, and 314, and means for locking the coupling-socket adapter against rotation with respect to the base plate subassembly and for unlocking the coupling-socket adapter for rotation with respect to the base plate subassembly, wherein the rotational locking and unlocking means is operable when the base plate subassembly is attached to the first prosthetic limb component. The base plate subassembly is attachable to a first prosthetic limb component. The coupling-socket adapter is rotatably attached to the base plate subassembly and has a cavity 124, 224, and 324 for receiving a male coupling member. The rotational locking and unlocking means are operable when the base plate subassembly is attached to the first prosthetic limb component. The rotational locking and unlocking means may include a ring 116 and 216 and/or a ring clamp 316, as previously described, or may include a coupling-socket adapter having a circumferential flange with a circumferential array of longitudinally-extending threaded holes for set screws to engage a corresponding circumferential flange on the top surface of the slide plate, and the like.

In the third broad expression of the invention, the base plate subassembly may include a base plate and a slide plate, as previously described, or may include a slide plate which slides in a surface groove of the first prosthetic limb component, or may lack a slide plate, etc. Also, the coupling-socket adapter may be rotatably attached to the base plate subassembly by using a threaded fastener, as previously described, or by using any other rotational attachment, as is within the level of skill of the artisan. When a threaded fastener is used, it need not have a tapered portion as long as it is not capable of passing completely through the hole of the base plate subassembly. It is noted that when a base plate and a slide plate are present, the ring must bottom out on the slide plate and not on the base plate to maintain independence of the rotational and sliding features, as can be appreciated by the artisan. As can be understood by those skilled in the art, the rotational locking and unlocking property of the ring can also be achieved by replacing (or supplementing) the threads of the coupling-socket adapter with threads on the base plate subassembly.

In the third broad expression of the invention, preferably, the base plate subassembly 112, 212, and 312 includes a hole (such as, but not limited to, a tapered hole 146, 246, and 346) having a longitudinal axis 162, 262, and 362. Preferably, the coupling-socket adapter 114, 214, and 314 is rotatably attached to the base plate subassembly through the hole. Preferably, the rotational locking and unlocking means longitudinally moves the coupling-socket adapter, relative to the base plate subassembly, in a first direction for locking the coupling-socket adapter against rotation with respect to the base plate subassembly and longitudinally moves the coupling-socket adapter, relative to the base plate subassembly, in a direction opposite to the first direction for unlocking the coupling-socket adapter for rotation with respect to the base plate subassembly.

It is noted, but not shown in the figures, that for any of the above-described expressions and embodiments of the invention, the base plate may include a stop pin located at each end of the surface groove to prevent the slide plate from escaping from the base plate which could lead to loss of the slidable member 142, 242, and 342. Also, the base plate may include a clearance through-hole 166, 266, and 366 exposing the bottom of the slide plate allowing, for example, clearance room for the tip of a locking pin of an inner sleeve of a prosthetic limb, as can be appreciated by the artisan. Although not shown, the ring 116 and 216 and/or coupling-socket adapter 114 and 214 may include flats or indentations (not shown) to enable various wrenches to grip the ring for rotation and counterrotation of the ring with respect to the coupling-socket adapter. Likewise, the threaded fastener 116 may include a bottom hexagonal recess to receive a wrench, and the threaded fasteners 216 and 316 may include 180-degree-apart bottom indentations to receive a wrench.

In the alternative, the previously-described first, second, and third preferred embodiments can be collectively described, in a fourth broad expression of the invention, as a coupling-socket adapter assembly 110, 210, and 310, for a prosthetic limb, which includes a base plate subassembly 112, 212, and 312, a coupling-socket adapter 114, 214, and 314, and a threaded press. The base plate subassembly 112, 212, and 312 is attachable to a first prosthetic limb. The coupling-socket adapter 114, 214, and 314 is positioned adjacent to the base plate subassembly. One of the base plate subassembly and the coupling-socket adapter includes a conical cavity that widens with the distance from the other one of the base plate subassembly and the coupling-socket adapter. The other one of the base plate subassembly and the coupling-socket adapter includes a conical projection extending therefrom and into the conical cavity, the conical projection widens with the distance from the other one of the base plate subassembly and the coupling-socket adapter. The threaded press is operative to push the base plate subassembly away from the coupling-socket adapter, thereby causing the conical projection to frictionally lock against the inner surface of the conical cavity, whereby the coupling-socket adapter is rotatable with respect to the base plate subassembly when the threaded press is deactivated, but is rotationally locked with respect to the base plate subassembly when the threaded press is activated.

In one embodiment, the threaded press is the ring 116, the conical cavity is the tapered hole 146, and the conical projection is the tapered portion 148 of the threaded fastener 118, all as previously described, wherein the threaded fastener is here considered a part of the coupling-socket adapter. In another embodiment, the threaded press is the ring 216, the conical cavity is the tapered hole 246, and the conical projection is the tapered portion 248 of the threaded fastener 218, all as previously described, wherein the threaded fastener is here considered a part of the coupling-socket adapter. In a further embodiment, the threaded press is the ring-clamp 316, the conical cavity is the tapered hole 346, and the conical projection is the tapered portion 348 of the threaded fastener 318, all as previously described, wherein the threaded fastener is here considered a part of the coupling-socket adapter. As can be appreciated by the artisan, in other embodiments, not shown, the coupling-socket adapter can have the conical cavity, and/or other threaded presses can be employed.

Several benefits and advantages are derived from the invention. Rotatably attaching a coupling-socket adapter to a base plate subassembly and providing a mechanism, such as the previously-described ring or ring-clamp, allows rotatable adjustment, including infinite rotational adjustments, for the prosthetic limb while the coupling-socket adapter assembly remains attached to the first prosthetic limb component. The ring does not significantly increase the profile or height of the attachment of the interconnection components. When present, the optional slide plate and optional slide locking and unlocking device of the base plate subassembly allow translational adjustment, including infinite translational adjustment, along a linear axis between two end positions for the prosthetic limb while the coupling-socket adapter assembly remains attached to the first prosthetic limb component.

The foregoing description of several expressions and preferred embodiments of the invention has been presented for purposes of illustration. It is not intended to be exhaustive or to limit the invention to the precise form and process disclosed, and obviously many modifications and variations are possible in light of the above teaching. It is intended that the scope of the invention be defined by the claims appended hereto.

What is claimed is:

1. A coupling-socket adapter assembly, for a prosthetic limb, comprising:
   a) a base plate subassembly attachable to a first prosthetic limb component;
   b) a coupling-socket adapter rotatably attached to the base plate subassembly, having an upper portion and a lower portion, and having a cavity for receiving a male coupling member, wherein the lower portion includes a tapered outside circumferential surface; and
   c) an adjustable-diameter ring clamp disposed between the base plate subassembly and the upper portion of the coupling-socket adapter and having a tapered inside circumferential surface which surround the tapered outside circumferential surface of the lower portion of the coupling-socket adapter, wherein decreasing the diameter of the ring clamp locks the coupling-socket adapter against rotation with respect to the base plate subassembly, and wherein increasing the diameter of the ring clamp unlocks the coupling-socket adapter for rotation with respect to the coupling-socket adapter.

2. The coupling-socket adapter assembly of claim 1, wherein the ring clamp and the coupling-socket adapter are keyed to prevent rotation relative to each other.

3. The coupling-socket adapter assembly of claim 1, wherein the base plate subassembly includes:
   a) a base plate attachable to the first prosthetic limb component and having a rectilinear surface groove;
   b) a slide plate slidably captured in the surface groove, wherein the coupling-socket adapter is rotatably attached to the slide plate, and wherein the ring is disposed between the base plate and the upper portion of the coupling-socket adapter; and
   c) means for locking the slide plate against sliding in the surface groove and for unlocking the slide plate for sliding in the surface groove, wherein the slide-plate locking and unlocking means is operable when the base plate is attached to the first prosthetic limb component.

4. The coupling-socket adapter assembly of claim 3, wherein there is play between the ring-clamp and the base plate for the rotationally-locked coupling-socket adapter and for the rotationally-unlocked coupling-socket adapter.

5. The coupling-socket adapter assembly of claim 3, wherein the surface groove is a dovetail-shaped surface groove, and wherein the slide plate is a dovetail-shaped slide plate.

6. The coupling-socket adapter assembly of claim 3, wherein the slide-plate locking and unlocking means includes the base plate having an internally-threaded hole and also includes a set screw threadably disposed in the internally-threaded hole of the base plate.

7. The coupling-socket adapter assembly of claim 1, wherein the coupling-socket adapter includes a plurality of internally-threaded holes having an outside end disposed in the upper portion of the coupling-socket adapter and having an inside end in communication with the cavity of the coupling-socket adapter, and also including a plurality of set screws threadably disposed in a corresponding internally-threaded hole of the coupling-socket adapter.

8. The coupling-socket adapter assembly of claim 7, wherein the internally-threaded holes of the coupling-socket adapter are angled towards the lower portion of the coupling-socket adapter as one moves inward in the internally-threaded holes of the coupling-socket adapter towards the cavity of the coupling-socket adapter.

9. The coupling-socket adapter assembly of claim 1, wherein the first prosthetic limb component is a knee joint assembly.

10. The coupling-socket adapter assembly of claim 3, wherein the base plate includes a plurality of countersunk holes for bolted attachment of the base plate to the first prosthetic limb component.

11. The coupling-socket adapter assembly of claim 1, wherein the base plate subassembly includes a tapered hole, and also including a threaded fastener threadably attached to the coupling-socket adapter and having a tapered portion disposed in the tapered hole.

12. The coupling-socket adapter assembly of claim 3, wherein the slide plate includes a tapered hole, and also including a threaded fastener threadably attached to the coupling-socket adapter and having a tapered portion disposed in the tapered hole.

13. The coupling-socket adapter assembly of claim 12, wherein the tapered portion has internal threads, wherein the lower portion of the coupling-socket adapter has external threads, and wherein the internal threads of the tapered portion are threadably engaged with the external threads of the lower portion.

14. The coupling-socket adapter assembly of claim 13, wherein the tapered portion is an entire portion of the threaded fastener.

15. The coupling-socket adapter assembly of claim 14, wherein the slide plate has a top surface facing the ring, and wherein the top surface is a substantially planar surface.

16. The coupling-socket adapter assembly of claim 15, wherein the cavity of the coupling-socket adapter is disposed partially in the upper portion of the coupling-socket adapter and partially in the lower portion of the coupling-socket adapter.

17. A coupling-socket adapter assembly for a prosthetic limb, comprising:
(a) a base plate subassembly attachable to a first prosthetic limb component;
(b) a coupling-socket adapter positioned adjacent to the base plate subassembly;
  (1) a first one of the base plate subassembly and the coupling-socket adapter including a conical cavity that widens with the distance from a second one of the base plate subassembly and the coupling-socket adapter;
  (2) the second one of the base plate subassembly and the coupling-socket adapter including a conical projection extending therefrom and into the conical cavity, the conical projection widens with the distance from the second one of the base plate subassembly and the coupling-socket adapter; and
(c) a threaded press, operative to push the base plate subassembly away from the coupling-socket adapter, thereby causing the conical projection to frictionally lock against the inner surface of the conical cavity, the threaded press comprising an adjustable-diameter ring clamp disposed between the base plate subassembly and an upper portion of the coupling socket adapter and having a tapered inside circumferential surface which surrounds the tapered outside circumferential surface of a lower portion of the coupling-socket adapter, wherein decreasing the diameter of the ring clamp locks the coupling-socket adapter against rotation with respect to the base plate subassembly, and wherein increasing the diameter of the ring clamp unlocks the coupling-socket adapter for rotation with respect to the base plate subassembly;
whereby the coupling-socket adapter is rotatable with respect to the base plate subassembly when the threaded press is deactivated, but is rotationally locked with respect to the base plate subassembly when the threaded press is activated.

\* \* \* \* \*

UNITED STATES PATENT AND TRADEMARK OFFICE
CERTIFICATE OF CORRECTION

PATENT NO. : 6,458,163 B1
DATED : October 1, 2002
INVENTOR(S) : Tracy C. Slemker, Lanny K. Wiggins and Scott R. Schall It is certified that error appears in the above-identified patent and that said Letters Patent is hereby corrected as shown below:

<u>Title page,</u>
Item [73], Assignee, the following entity should be added as a joint-assignee:
-- Ca-Tech, Inc., Centerville, OH --

<u>Column 1,</u>
Line 65, "gate" should be -- gait --

Signed and Sealed this

Eighteenth Day of February, 2003

JAMES E. ROGAN
*Director of the United States Patent and Trademark Office*